(12) United States Patent
Eckert

(10) Patent No.: US 7,645,765 B2
(45) Date of Patent: Jan. 12, 2010

(54) USE OF MOXAVERIN FOR TREATING ERECTILE DYSFUNCTION, FORMS OF DEMENTIA OR DISEASES ASSOCIATED TO AN ARTERIOSCLEROTIC OCCLUSION

(75) Inventor: Ralph E. Eckert, Homburg (DE)

(73) Assignee: Molecular and Clinical Drug Research, Lebach (DE)

( * ) Notice: Subject to any disclaimer, the term of this patent is extended or adjusted under 35 U.S.C. 154(b) by 728 days.

(21) Appl. No.: 10/512,670

(22) PCT Filed: Sep. 2, 2002

(86) PCT No.: PCT/EP02/09777

§ 371 (c)(1),
(2), (4) Date: Oct. 26, 2004

(87) PCT Pub. No.: WO03/018016

PCT Pub. Date: Mar. 6, 2003

(65) Prior Publication Data

US 2005/0208081 A1      Sep. 22, 2005

(30) Foreign Application Priority Data

Aug. 31, 2001   (DE) ................................ 101 42 418

(51) Int. Cl.
*A61K 31/435*   (2006.01)
*A61K 31/44*   (2006.01)

(52) U.S. Cl. ...................................... 514/277; 514/299
(58) Field of Classification Search ................. 514/299, 514/277
See application file for complete search history.

(56) References Cited

U.S. PATENT DOCUMENTS 4,018,927 A * 4/1977 Voorhees .................... 514/307
6,124,461 A * 9/2000 Shoemaker ................. 546/147

FOREIGN PATENT DOCUMENTS

WO      WO 97/21457      6/1997
WO      WO 00/15233      3/2000

OTHER PUBLICATIONS

Girgis, E. Ion-pair reversed-phase liquid chromatographic identification and quantitation of papaverine congeners. Journal of Pharmaceutical Sciences, vol. 82, No. 5, May 1993, pp. 903-905.*
International Search Report.

* cited by examiner

*Primary Examiner*—Sreeni Padmanabhan
*Assistant Examiner*—Renee Claytor
(74) *Attorney, Agent, or Firm*—Collard & Roe, P.C.

(57) ABSTRACT

The invention relates to a drug containing an aqueous formulation of Moxaverin and at least one water-miscible solubilizer.

13 Claims, No Drawings

USE OF MOXAVERIN FOR TREATING ERECTILE DYSFUNCTION, FORMS OF DEMENTIA OR DISEASES ASSOCIATED TO AN ARTERIOSCLEROTIC OCCLUSION

CROSS REFERENCE TO RELATED APPLICATIONS

Applicant claims priority under 35 U.S.C. §119 of German Application No. 101 42 418.3 filed Aug. 31, 2001. Applicant also claims priority under 35 U.S.C. §365 of PCT/EP02/09777 filed Sep. 2, 2002. The international application under PCT article 21(2) was not published in English.

The invention relates to a medication that contains moxaverin as an active ingredient. The invention furthermore relates to formulations of moxaverin, as well as the use of moxaverin for the production of medications.

Moxaverin is a further development of the active substance papaverin, and acts as a musculotropic spasmolytic that is 2.5× more effective than the parent substance papaverin.

As experimental studies have shown, the substance is ten times less toxic than papaverin, after oral administration. In this connection, the muscle-relaxing effect is based on the inhibition of phosphodiesterase (PDE) and the resulting increase in the cyclic AMP level (cAMP) in the smooth muscle cells. Furthermore, moxaverin causes an increase in erythrocyte flexibility and results in the inhibition of thrombocyte aggregation.

Until now, spasms and cramps in the gastrointestinal tract, in the gall bladder and in the ureter, menstrual cramps, peripheral and cerebral arterial as well as coronary circulation problems were known as indications. Furthermore, because of its properties of promoting blood flow, moxaverin is also used in the treatment of vascular forms of dementia.

According to clinical studies, moxaverin is connected with a good clinical efficacy and, at the same time, a high level of drug safety, even within the framework of high-dose, long-term therapy.

In this connection, moxaverin (1-benzyl-3-ethyl-6,7-dimethoxyisoquinoline, $M_r$ 307.38) is used both in the form of the free base and in the form of the hydrochloride (moxaverin HCl, $M_r$ 343.9). Since the substance is hardly soluble in water, it is administered almost exclusively in an ethanol formulation. Such ethanol formulations have a pH of approximately 3.5 to 4.

Oral administration of ethanol formulations is generally non-problematic (with the exception of the treatment of alcohol addicts), but oral therapy is not suitable for all indications, for example because of the poor bioavailability of the administered drug as compared with intravenous administration. Therefore parenteral administration (e.g. intravenous or intramuscular) of 0.03 to 0.15 g moxaverin per dose in ethanol solution is also known. The administration of such injections, however, is connected with significant pain, due to the venotoxicity of the non-physiological solvent and the non-physiological pH of the formulation.

It is true that aqueous moxaverin HCl solutions having a physiological pH can be produced, but medicinal formulations on the basis of such solutions demonstrate too low a concentration of moxaverin HCl (maximum 1 mg/ml) to achieve a noteworthy medicinal effect, because of the extremely low water solubility of moxaverin HCl. Also, this low concentration of moxaverin would be difficult to compensate by means of the administration of larger volumes. In addition, the stability of active substances in highly concentrated solutions is generally greater than in solutions having a low concentration. In the form of the free base, moxaverin is practically insoluble in water (<1 mg/ml).

There is therefore a need for medications with liquid formulations of moxaverin that are better tolerated as compared with those known from the state of the art.

This task is accomplished, according to the invention, by means of a medication that contains an aqueous formulation of moxaverin with at least one solubilizer that is miscible with $H_2O$.

The invention comprises medications for the treatment of humans as well as veterinary drugs.

The invention is based on the surprising result that when using at least one solubilizer that is miscible with $H_2O$, it is possible to obtain aqueous, highly concentrated formulations with moxaverin. In this connection, the moxaverin is mixed with the solubilizer that is miscible with $H_2O$, brought into solution, and subsequently adjusted to the desired concentration. Surprisingly, the moxaverin remains in solution even after dilution with water, and retains its smooth-muscle-relaxing activity.

The aqueous formulations of moxaverin according to the invention are physiologically better tolerated than ethanol formulations at a comparable concentration, since no ethanol-related painful tissue damage occurs when injecting the medication according to the invention.

Since the administration of the medication according to the invention does not cause any pain, greater volumes of liquid moxaverin formulations can be applied, which demonstrate similarly high concentrations as ethanol solutions. In total, far greater individual doses can be administered in this way.

Therefore it can be assumed that a clear increase of the therapeutic benefit for the known indications of moxaverin, such as peripheral arterial or coronary occlusion disease, vascular-related dementia, etc., can be achieved.

In addition, the medication according to the invention, on the basis of the new type of formulation, demonstrates a broad spectrum of use as compared with medications on the basis of the known ethanol formulations. Thus, highly concentrated moxaverin solutions based on water can be administered orally even to alcohol addicts, without risk. In particular, it is now possible to use not only systemic administration by means of intravenous injections, but also local injections.

In this connection, the medication according to the invention can fundamentally be present in any form of administration that is suitable for administering aqueous moxaverin solutions. For example, medications for oral, ocular, rectal, and parenteral (e.g. subcutaneous, intramuscular, intravenous, intracavernous, etc.) administration are possible; the best-suited form of administration is, however, dependent on the type and severity of the pathological state to be treated. For example, drops for oral administration or eye drops are just as possible as aqueous gels or soft capsules having an at least partially liquid content. Particularly preferred embodiments are injection solutions, since the injection solutions containing moxaverin that are known from the state of the art are particularly unsatisfactory with regard to physiological tolerance, on the one hand, and therapeutic efficacy, on the other hand.

The term moxaverin includes the active substance both as a free base and as a pharmaceutically tolerated salt, ester, amide, as well as any type of physiologically tolerated moxaverin derivative. Pharmaceutically tolerated salts are salts that are produced from pharmaceutically tolerated, non-toxic acids of moxaverin; the preferred example here is moxaverin hydrochloride. Moxaverin in the form of the free base demonstrates the advantage that the pH is not too low, in and of itself, in the production of the aqueous formulation. When using moxaverin hydrochloride, on the other hand, the production of moxaverin solutions having a particularly high concentration is possible, since the hydrochloride in and of itself is already soluble in water, to a slight degree.

Solubilizers are substances that improve the solubility of other substances. In this connection, solubilization can take place on the basis of complexing, by means of molecular variation and salt formation, by means of micelle formation (solubilization), or by means of improving the solution conditions as a result of structural changes of the solvent (co-solvatization). According to the invention, co-solvents of water (i.e. organic solvents that are miscible with water in any desired manner), with the exception of ethanol, are preferably used as solubilizers. In this connection, fundamentally any solubilizers that are suitable for the production of medications and in which moxaverin is well soluble (i.e. better soluble than in water, preferably at least as well soluble as in ethanol), and that are miscible with water, can be used as solubilizers.

According to a preferred embodiment, at least 0.5 mg/ml, preferably at least 1 mg/ml moxaverin are contained in the aqueous solution. Such concentrations have traditionally been obtained only in ethanol solution, not in normal aqueous solution.

According to a preferred embodiment, a polyalkylene glycol or a mixture of different polyalkylene glycols is used as the solubilizer. Polyalkylene glycols from the group of polypropylene glycols or polyethylene glycols are particularly suitable in this connection, because of the physiological tolerance. In this connection, the use of polyethylene glycols is preferred. Polyethylene glycols are characterized by their good tolerance and their excellent solution properties, while having unlimited miscibility in water.

For the production of the medication according to the invention, polyethylene glycols with average molecular weights (weight mean) between 200 and 2000 are possible, since these are essentially liquid at room temperature. In this connection, the production of particularly highly concentrated aqueous moxaverin solutions is possible with polyethylene glycols having an average molecular weight of 200 (PEG 200) to 400 (PEG 400). Accordingly, the use of PEG 400 as a solubilizer is particularly preferred.

Because of their good solution properties, with good tolerance, the use of aqueous polyvinyl pyrrolidine (PVP) solutions at PVP concentrations that are suitable for the production of medicinal solutions, as a solubilizer, can also be practical.

Because of the maximum solubility of approximately 40 mg/ml moxaverin in undiluted PEG and the permissible upper limits of 30% PEG in medications, the maximum moxaverin concentration that can be achieved in the finished aqueous medicinal solution, when using PEG as the solubilizer, is on the order of approximately 12 mg/ml.

The medication according to the invention can contain other usual formulation substances and additives, in addition to the stated substances (depending on the form of the medication, in each instance, and the indication, in each instance). Since the use of the lowest possible number of additives minimizes the risk of side effects, the medication according to the invention has the least possible number of additives. This purpose is also benefited if the aqueous formulation of the medication according to the invention contains only a single solubilizer, preferably polyethylene glycol (particularly PEG 400).

In order to minimize the risk of adverse effects and obtain formulations having as low a viscosity as possible, it is practical if the content of solubilizer in the finished aqueous solution is as low as possible. It is therefore practical if the content of polyethylene glycol in the aqueous formulation is a maximum of 30 vol.-%, but preferably less.

In this connection, it can be practical, depending on the indication, if one or more additional medicinally active ingredients is/are contained in the medication according to the invention. In this connection, the medicinally active ingredients can be contained in a formulation other than an aqueous one (e.g. in the case of gel capsules, which contain an aqueous formulation of moxaverin, among other things). Preferably, however, they are also contained in the aqueous formulation. In this connection, all substances that are not contraindicated when administering moxaverin, and develop medicinal effects that demonstrate an additive or synergistic conduct with regard to the effect of moxaverin, are fundamentally possible as medicinally active ingredients. These can be substances having a different pharmacological effect than that of moxaverin (in the sense of a supplementary effect), but also those with essentially the same or a similar pharmacological effect (e.g. antihypertensive drugs and/or those that promote blood circulation). Preferably, one or more substances from the group of α-receptor antagonists (α-receptor blockers), PDE inhibitors and/or Ca antagonists is/are used as additional medicinal ingredients.

According to a particularly preferred embodiment of the medication, the aqueous formulation has an essentially physiological pH of between 6.0 and 8.0, preferably between 7.0 and 8.0, particularly preferably between 7.3 and 7.5, and especially approximately 7.4. Such formulations, having an essentially physiological pH, are characterized by particularly good tolerance when administered parenterally, and injecting them is not connected with pH-related venotoxicity. The production of such aqueous formulations having an essentially physiological pH takes place by means of adjusting the pH using a conventional physiological buffer suitable for the production of medicinal solutions, after the moxaverin is dissolved and then diluted to the desired end concentration. In this connection, it has surprisingly been shown that moxaverin in the medication according to the invention is stable and active both in its form as a free base and in its form as a hydrochloride, even after adjustment of an essentially physiological pH, and does not precipitate.

In this form, the medication according to the invention is suitable for use within the scope of a particularly great spectrum of different indications. Thus, injections of moxaverin, for example systemic intravenous, but also local as well as intracavernous injections, are now possible, without pain, in addition to oral administration. Furthermore, such aqueous, pH-neutral formulations of moxaverin can also be used as eye drops, without resulting in local irritation.

The concentration of moxaverin in the medication, in each instance, and the total amount of moxaverin administered per dose depends, in individual cases, on the form of administration, in each instance (gel capsule, eye drops, injection solution, etc.), the indication, and the severity of the pathological state to be treated. For intravenous, systemic administration of moxaverin, e.g. within the framework of therapy for a stroke, high individual doses are desired, with concentrations of moxaverin of 12 mg/ml and more. In the case of intracavernous injection into the erectile tissue, individual doses of preferably 1 to 10 mg, applied in the smallest possible volume, e.g. in 1 ml injection solution, are practical.

According to a particularly practical embodiment, the aqueous formulation of the medication according to the invention has an essentially isotonic and, preferably, an isotonic setting (i.e. an at least essentially isotonic electrolyte concentration and/or an at least essentially isotonic electrolyte composition). This can take place, for example, by means of an adjustment with physiological saline solution, with conventional Tyrode's buffers, or other buffers suitable for the production of medicinal solutions, as known to a person skilled in the art.

A method in which the medicinally active ingredient(s) is/are dissolved in undiluted solubilizer, preferably in polyalkylene glycol and, particularly preferably, in polyethylene glycol, followed by the addition of a suitable buffer for adjusting an essentially physiological pH and/or an essentially isotonic electrolyte content with reference to the final dilution of the aqueous formulation, as well as the addition of $H_2O$ or aqueous buffer solution to achieve the end volume, is suitable for the production of the aqueous formulation of the medication according to the invention.

It has been shown that the production of the aqueous solution is practical in undiluted polyethylene glycol, in a temperature range between 16 and 40° C., and preferably at approximately 37° C. At these temperatures, moxaverin dissolves in polyethylene glycols particularly well, and here, in particular, this also applies to polyethylene glycols in the range of an average relative molecular weight between 200 and 600.

Because of the aqueous formulation of its active ingredient, the medication is fundamentally suitable for all applications. In contrast to liquid formulations based on a non-physiological solvent, it is furthermore suitable, however, for all forms of administration for which liquid formulations of moxaverin based on ethanol are unsuited or connected with disadvantages.

By means of the advantages connected with the new galenics, as compared with conventional aqueous or ethanol formulations of moxaverin, the medication according to the invention allows the use of moxaverin within the scope of new indications. Thus it is now possible, on the basis of the improved properties as compared with known medications containing moxaverin, to use moxaverin locally for the treatment of erectile dysfunction, for example, but also in intraocular manner, to improve blood circulation in the retina, particularly for diabetics, patients with hypertension, and MS patients.

For the treatment of erectile dysfunction with moxaverin, it is necessary to administer moxaverin locally. Here, local injections, e.g. intraurethral and particularly intracavernous injections, are particularly effective. Since it is not possible to inject simply any desired volume in intracavernous manner, a minimum concentration of 0.5 mg/ml, preferably, however, 1 mg/ml moxaverin, must be present in the formulation, in order to administer a sufficient absolute amount of moxaverin. Such concentrations cannot be achieved with the conventional aqueous formulations.

The highly concentrated ethanol formulations, on the other hand, are not suitable for intracavernous administration, because of the pain caused by injecting them. The medication according to the invention, on the other hand, does not demonstrate any of these disadvantages: according to a preferred embodiment, the medication according to the invention is therefore suitable for the treatment of erectile dysfunction.

The invention furthermore relates to the aqueous formulations of moxaverin as described above, as well as their use for the production of medications. Another object of the invention is injection solutions based on the aqueous formulations of moxaverin. With regard to the treatment of erectile dysfunction, in this connection injection solutions are preferred that are intended for local injection, e.g. for intraurethral and particularly for intracavernous injection. For the treatment of other pathological states, on the other hand, other injection solutions, for example for intravenous or intramuscular administration, can be practical.

Because of the new and, as compared with known formulations, improved properties of the formulation of moxaverin according to the invention, it is now possible to use moxaverin for the local treatment of erectile dysfunction. The invention therefore relates also to the use of moxaverin for the production of medications for the treatment of erectile dysfunction.

According to a particularly practical embodiment, such a medication for the treatment of erectile dysfunction contains an aqueous formulation with between 1 to 10 mg moxaverin hydrochloride per 1 ml end volume as the active ingredient, and furthermore contains a maximum of 12.5%, preferably less, however, polyethylene glycol having an average molecular weight of 400 weight average, and has a pH of approximately 7.4.

In the following, the invention will be explained using examples.

EXAMPLE 1

Production of an Injection Solution Containing Moxaverin 400 mg moxaverin hydrochloride were dissolved in 10 ml PEG 400 (manufactured by Sigma) while stirring constantly, on a hot plate, at 37° C. After complete dissolution, 4 ml 10× concentrated Tyrode's solution were added, and then 2M NaOH was dripped in, in order to adjust the pH, while stirring and constantly monitoring the pH, until a pH of 7.4 had been reached. Subsequently, the volume was filled up with twice-distilled $H_2O$, to a volume of 40 ml. It was possible to use the finished master solution with 10 mg/ml moxaverin HCl, pH=7.4, and an isotonic electrolyte concentration directly, after sterile filtration, or to first dilute it further to a desired moxaverin concentration, using 1× Tyrode's solution.

EXAMPLE 2

Solubility of Moxaverin Hydrochloride in Aqueous Solutions Containing Polyethylene Glycol Moxaverin hydrochloride was dissolved completely, as a pure substance, in increasing mass proportions (see Table 1), in 10 ml commercially available polyethylene glycol having an average molecular weight of 200 and 400, respectively (manufactured by Sigma, PEG 200 and 400, <1% $H_2O$), while stirring constantly, at a temperature of 37° C. In this connection, it was possible to achieve moxaverin concentrations of up to 40 mg/ml in undiluted polyethylene glycol 400. (For a comparison: in EtOH, a maximum of 200 mg/ml moxaverin hydrochloride can be brought into solution, and in $H_2O<1$ mg/ml.)

Subsequently, the dissolved moxaverin was converted to an aqueous solution, while stirring constantly, by adding 1×Tyrode's solution with a normal extracellular electrolyte composition. It was possible to dilute the solutions as desired, without the dissolved moxaverin precipitating.

To determine the pH dependence of the solution behavior of moxaverin hydrochloride, a pH of 7.4 was adjusted in another series of experiments, after complete dissolution in undiluted PEG, by adding NaOH.

As is evident from Table 1, the moxaverin HCl dissolved in PEG 200 precipitated at concentrations of 35 mg/ml and more, after neutralization. The moxaverin dissolved in PEG 400, on the other hand, remained in solution at high concentrations, even after pH neutralization. It was also possible to dilute the pH-neutral moxaverin solutions produced in this manner in any desired manner. The moxaverin did not precipitate even at low PEG concentrations of 5% and less. The moxaverin HCl dissolved in it was active. The solutions remained stable for more than six months, without precipitation of the moxaverin.

In comparison, an attempt was made to dissolve moxaverin HCl in 5-10% PEG diluted with H₂O and Tyrode's solution, respectively. (In other words, analogous to the series of experiments shown in the table, 15 to 40 mg moxaverin HCl were added to 10 ml 10% PEG 400, or 7.5 to 20 mg moxaverin HCl were added to 10 ml 5% PEG 400, and stirred at 37° C.) However, directly dissolving the pure substance in diluted PEG was not possible either in diluted PEG 400 or in diluted PEG 200.

EXAMPLE 3

Patient Study

Twenty patients having a completely clarified genesis of erectile dysfunction were given intracavernous injections (injection therapy of erectile tissue) of aqueous solutions of moxaverin. In this connection, 1 ml of an injection solution containing 1 to 10 mg moxaverin hydrochloride per ml end volume, in Tyrode's buffer, at a pH=7.4 and an end concentration of 2.5% PEG 400 (in the case of 1 mg moxaverin HCl/ml) up to 25% PEG 400 (in the case of 10 mg moxaverin HCl/ml) were administered per individual injection.

In more than 90% of the cases, it was possible to provoke a sufficiently strong penile erection with a degree of erection E=4-5 (using a scale from 0 to 5) in this manner. No pain was observed in connection with the injection. Side effects such as priapism were also not observed. In this study, the use of moxaverin in the treatment of erectile dysfunction resulted in elimination of the pathological symptoms, with simultaneous absence of adverse side effects.

2. The medication according to claim 1, wherein the content of solubilizer in the aqueous formulation is a maximum of 30 percent by volume of the aqueous formulation.

3. The medication according to claim 1, wherein the polyalkylene glycol(s) is/are polypropylene glycols and/or polyethylene glycols.

4. The medication according to claim 3, wherein the aqueous formulation contains polyethylene glycols having an average molecular weight between 200 and 2000.

5. The medication according to claim 4, wherein the aqueous formulation contains polyethylene glycols having an average relative molecular weight of 400.

6. The medication according to claim 1, wherein it contains one or more additional medicinally active ingredients.

7. The medication according to claim 6, wherein one or more substances from the group of α-receptor antagonists, α-receptor blockers, PDE inhibitors and/or Ca antagonists is/are contained as additional medicinal ingredients.

8. A medication comprising an aqueous formulation of moxaverine hydrochloride, which is obtained by means of dissolving the moxaverine hydrochloride and the other medicinally active ingredient(s), if applicable, in undiluted solubilizer, adjusting a suitable pH, and dissolving to the end concentration with water;
   wherein the content of moxaverine hydrochloride in the aqueous formulation is at least 0.5 mg/ml; and
   wherein the aqueous formulation has a PH of between 6.0 and 8.0.

9. The medication according to claim 8, wherein dissolving of the moxaverine hydrochloride and/or the additional medicinally active ingredients takes place between 16 and 40° C.

10. The medication according to claim 1, wherein it is intended for parenteral administration.

TABLE 1

| Moxaverin | | | | | | |
|---|---|---|---|---|---|---|
| Solubility in 10 ml PEG 200, temperature 37° C. | | | | | | |
| Mass | 150 mg | 200 mg | 250 mg | 300 mg | 350 mg | 400 mg |
| pH | 3.05 | 3.06 | 2.97 | 2.95 | 2.87 | 2.75 |
| Solubility at pH 7.4 | Yes | Yes | Yes | Yes | No | No |
| Solubility in 10 ml PEG 400, temperature 37° C. | | | | | | |
| Mass | 150 mg | 200 mg | 250 mg | 300 mg | 350 mg | 400 mg |
| pH | 2.53 | 2.33 | 2.27 | 2.30 | 2.22 | 2.12 |
| Solubility at pH 7.4 | Yes | Yes | Yes | Yes | Yes | Yes |
| Solubility test of moxaverin in ethanol, temperature 26.6° C., pH meter calibrated, moxaverin HCl, ethanol (pharmacy) 90% | | | | | | |

| Mass | 10 mg/ml | 20 mg/ml | 30 mg/ml | 40 mg/ml | 50 mg/ml | 60 mg/ml | 100 mg/ml | 200 mg/ml |
|---|---|---|---|---|---|---|---|---|
| pH | 3.49 | 3.36 | 3.30 | 3.19 | 3.13 | 3.11 | 3.00 | 2.96 |
| Solubility | Dissolved | Dissolved | Dissolved | Dissolved | Dissolved | Dissolved | Dissolved | Dissolved |

The invention claimed is:

1. A medication comprising an aqueous formulation of moxaverine hydrochloride with at least one solubilizer that is miscible with H₂O selected from polyalkylene glycols;
   wherein the content of moxaverine hydrochloride in the aqueous formulation is at least 0.5 mg/ml; and
   wherein the aqueous formulation has a pH of between 6.0 and 8.0.

11. The medication according to claim 1 comprising a plurality of aqueous formulations of moxaverine hydrochloride.

12. An injection solution comprising the medication according to claim 10.

13. The injection solution according to claim 12, for use in intravenous injections.

* * * * *

UNITED STATES PATENT AND TRADEMARK OFFICE
CERTIFICATE OF CORRECTION

PATENT NO. : 7,645,765 B2  Page 1 of 1
APPLICATION NO. : 10/512670
DATED : January 12, 2010
INVENTOR(S) : Ralph E. Eckert It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1157 days.

Signed and Sealed this

Sixteenth Day of November, 2010

David J. Kappos
*Director of the United States Patent and Trademark Office*